United States Patent [19]
Crosland

[11] Patent Number: 6,082,998
[45] Date of Patent: Jul. 4, 2000

[54] HAND-HELD DENTAL ARTICULATOR

[76] Inventor: Larry Crosland, 1056 W. Genesee St., Apt. 2A, Syracuse, N.Y. 13204-2262

[21] Appl. No.: 09/201,169

[22] Filed: Nov. 30, 1998

[51] Int. Cl.[7] .................................................. A61C 11/00
[52] U.S. Cl. ............................................... 433/54; 433/57
[58] Field of Search .................................. 433/54, 56, 57, 433/58, 60, 61, 66

[56] References Cited

U.S. PATENT DOCUMENTS

| 2,130,083 | 9/1938 | Franwick | 433/66 |
|---|---|---|---|
| 2,237,050 | 4/1941 | Franwick . | |
| 2,262,574 | 11/1941 | Chott . | |
| 2,644,233 | 7/1953 | Shmukler et al. . | |
| 2,884,696 | 5/1959 | Bonfanti | 433/57 |
| 2,928,175 | 3/1960 | Knoth | 433/60 |
| 5,015,182 | 5/1991 | Newberry | 433/60 |
| 5,380,199 | 1/1995 | Koutavas | 433/65 |
| 5,695,333 | 12/1997 | Atwood et al. | 433/57 |
| 5,743,733 | 4/1998 | Crosland | 433/57 |

*Primary Examiner*—Ralph A. Lewis
*Attorney, Agent, or Firm*—Trapani & Molldrem

[57] ABSTRACT

A hand-held dental articulator, comprising a first frame, a second frame, and a support structure coupled to the first and second frames. The first frame is configured to accept for fixation thereto a first dental model. The second frame is configured to accept for fixation thereto a second dental model. The support structure is configured to support the first frame in opposing and overlapping relationship with the second frame. The support structure includes a manual surface that substantially conforms to the curvature of an operator's palm, such that the articulator is easily and comfortably held in the operator's hand during use.

13 Claims, 4 Drawing Sheets

HAND-HELD DENTAL ARTICULATOR

BACKGROUND OF THE INVENTION

1. Technical Field

The present invention relates generally to dental appliances, and more particularly to dental articulators.

2. Background Art

A dental articulator is a device for mounting casts or models of a patient's upper and lower jaws, and for simulating the occlusion of the patient's jaws. Dental articulators are used by dental laboratory technicians to construct dental prostheses, such as dentures, crowns, bridges, etc. They are also used by dentists and dental schools for educational and demonstration purposes. Whatever the application, these devices are regularly held in the operator's hand for examination and/or adjustment of the casts. For example, a laboratory technician may typically handle an articulator for two or two-and-a-half hours during the process of setting up dentures. Such extensive handling of the articulator usually leads to fatigue, causing the operator to put the device down a number of times during a procedure. This obviously prolongs the procedure, making the operator less productive than if he or she could have completed the procedure without interruptions. In addition to fatigue, such extensive handling of articulators has lead to more permanent conditions, such as carpal tunnel syndrome.

Notwithstanding the extensive handling requirements of dental articulators, the designers of such devices have, heretofore, essentially ignored the consequences stemming from such handling. It is believed that such inattention has been due to the designers' preoccupation with trying to duplicate or approximate the anatomy of the jaws in the articulator. A reading of many prior patents disclosing articulators seems to supports such a belief. Anatomical considerations are not always consistent with ergonomic considerations. For example, U.S. Pat. No. 2,237,050 to Franwick, U.S. Pat. No. 2,262,574 to Chott, and U.S. Pat. No. 2,644,233 to Shmukler et al., all demonstrate an effort to simulate the anatomy of the jaws. However, the resulting designs are obviously not ergonomically optimized for extensive handling.

U.S. Pat. No. 5,015,182 to Newberry and certain product literature by Snap-Art Precision Dental Products, El Dorado Hills, Calif., disclose articulators, which are examples of some effort to deviate from the traditional anatomical designs and provide some ergonomic attributes to an articulator. Both examples include a single post which may be grasped by the operator during her work. However, in both examples, the post is generally straight, and thus would not conform, at least in the vertical dimension, to the curvature of the operator's palm. In addition, the post configuration requires the fingers to flex (or wrap) around the post to effectively secure the articulator in the hand.

U.S. Pat. No. 5,743,733 to Crosland (the same inventor as named herein) discloses a new type of articulator, which has been made known to the public by way of printed publication since 1996. This articulator also includes a post. One of the novel aspects of this articulator is that the position of the post is adjustable in different directions. The adjustable post is partially enclosed in a collar 48, which may be grasped by the operator when handling the articulator. The rear surface of the collar is, however, flat, and thus does not conform to the curvature of the operator's palm. As a result of Mr. Crosland's efforts to improve upon this articulator, the present invention was made.

OBJECTS AND SUMMARY OF THE INVENTION

It is therefore an object of the present invention to provide a hand-held dental articulator that avoids the problems associated with the prior art.

It is another object of the present invention to provide a hand-held dental articulator that is easy and comfortable to handle while performing most procedures with the articulator.

It is a further object of the present invention to provide a hand-held dental articulator that fits comfortably in the palm of an operator's hand.

It is yet another object of the present invention to provide a hand-held dental articulator that is easy to manipulate.

It is yet a further object of the present invention to provide a hand-held dental articulator that facilitates manual examination and manipulation of the patient's dental casts.

It is still another object of the present invention to reduce the manual fatigue of an operator while preforming lengthy articulator procedures.

It is still a further object of the present invention to improve the productivity of a dental lab technician by providing a hand-held dental articulator that is easy and comfortable to handle and easy to manipulate.

These and other objects are attained in accordance with the present invention wherein there is provided a hand-held dental articulator, comprising a first frame, a second frame, and a support structure coupled to the first and second frames. The first frame is configured to accept for fixation thereto a first dental model. The second frame is configured to accept for fixation thereto a second dental model. The support structure is configured to support the first frame in opposing and overlapping relationship with the second frame. The support structure includes a manual surface that substantially conforms to the curvature of an operator's palm, such that the articulator is easily and comfortably held in the operator's hand during use.

In the preferred embodiment, the manual surface of the support structure also conforms to the size of the operator's palm. The support structure includes a housing, and the manual surface of the support structure is a surface of the housing. The housing is configured and dimensioned to fit in the operator's palm.

In the preferred embodiment, the support structure further includes a positioning member and a clamp. The positioning member has one end coupled to the first frame. The positioning member extends through the clamp. The clamp allows for adjustment of the position of the positioning member, and secures the positioning member in an adjusted position. The position of the first frame relative to the second frame is adjustable by adjusting the position of the positioning member. The housing substantially encloses the positioning member and the clamp.

BRIEF DESCRIPTION OF THE DRAWING

Further objects of the present invention will become apparent from the following description of the preferred embodiment with reference to the accompanying drawing, in which.

DESCRIPTION OF THE PREFERRED EMBODIMENT

Figure 1:
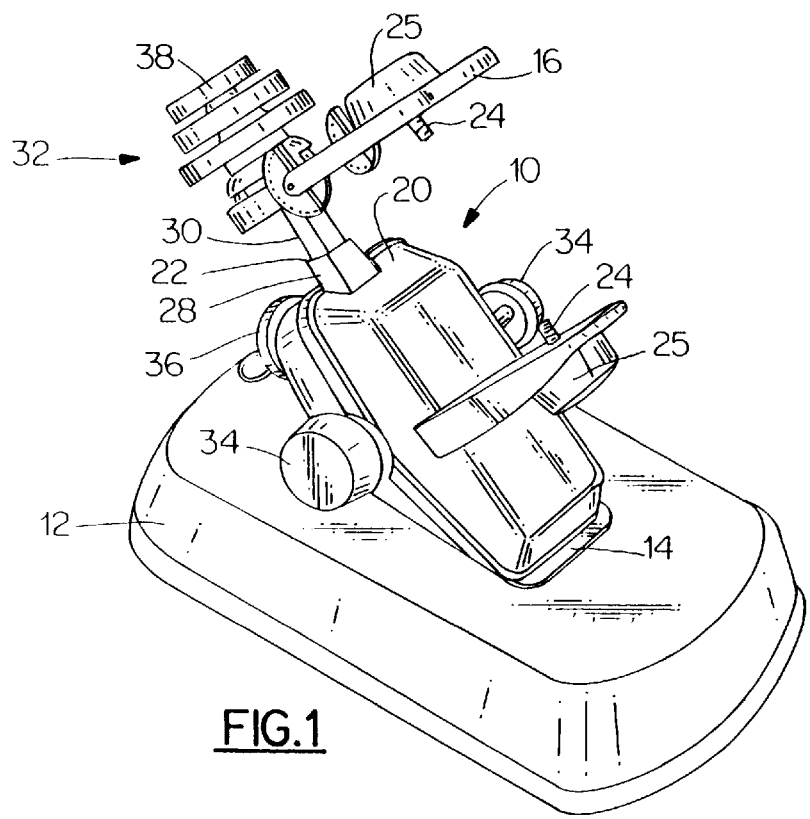
FIG. 1 is a perspective view of a hand-held dental articulator constructed in accordance with the present invention, shown resting in a base.

Referring now to FIG. 1, there is shown a hand-held dental articulator 10 constructed in accordance with the present invention. Articulator 10 is cradled in a base 12. Base 12 contains a recess 14 which is suitably shaped to support articulator 10 at about a 45 degree pitch. In this 45 degree orientation, the patient's dental casts (or models), which are to be mounted on articulator 10, can be conveniently viewed.

As shown in FIG. 1, articulator 10 comprises an upper mounting frame 16, a lower mounting frame 18, a housing 20, and a positioning member 22. In this embodiment, upper and lower mounting frames 16 and 18 each include a mounting screw 24 having a knob or head 25. Mounting frames 16 and 18 contain slotted holes 26 and 27, respectively (See FIGS. 4 and 5), through which screws 24 are inserted. Once inserted through their respective mounting frames, screws 24 are intended to be threaded into respective metal mounting plates (not shown) which form part of the patient's dental (or jaw) casts (or models). By this arrangement, the patient's upper and lower jaw models are mounted to upper and lower frames 16 and 18, respectively (See FIG. 3).

It should be noted that the present invention is not limited to any particular configuration for frames 16 and 18, or to any particular method of mounting the jaw models to frames 16 and 18. For example, frames 16 and 18 may be suitably configured to directly accept plaster mounted casts or models, in a well-known conventional manner.

With further reference to FIG. 1, positioning member 22 includes an outer positioning post 28 and a spring biased plunger 30. In this embodiment, positioning post 28 is configured as a square tube and plunger 30 slidably engages the inside of post 28 in a telescoping fashion (See also FIG. 5). As will be described in greater detail with respect to FIG. 5, plunger 30 forms part of a coupling arrangement between positioning member 22 and upper mounting frame 16. The coupling arrangement is designated generally in FIG. 1 by the reference number 32. Positioning member 22 is adjusted from side-to-side, within housing 20, by turning at least one of a pair of adjustment knobs 34. Front-to-back adjustment of positioning member 22 may be accomplished by turning an adjustment wheel 36, at the rear of housing 20 (See also FIG. 6). Positioning member 22 may be extended in length by turning an adjustment wheel 38.

In the preferred embodiment, housing 20, positioning member 22, and coupling arrangement 32, together, constitute a support structure to which frames 16 and 18 are attached. As seen from FIG. 1, the support structure is configured to support upper frame 16 in an opposing and overlapping relationship with lower frame 18. In accordance with the present invention, the support structure includes a "manual surface" (i.e., a surface intended to contact the palm of a hand) that substantially conforms to the curvature of a person's palm. In the preferred embodiment, the manual surface of the support structure is the rear surface of housing 20 (See FIGS. 8–10). This conformed surface allows articulator 10 to be easily and comfortably held in the palm of a hand during use (See FIGS. 2 and 3).

It should be noted that the present invention is not limited to any particular configuration for the support structure. For example, more conventional structures may be suitable, such as disclosed in U.S. Pat. No. 2,237,050 to Franwick: U.S. Pat. No. 2,262,574 to Chott: U.S. Pat. No. 2,644,233 to Shmukler et al.; and U.S. Pat. No. 5,015,182 to Newberry. However, such structures must be modified to include a manual surface that substantially conforms to the curvature of a person's palm.

Figure 2:
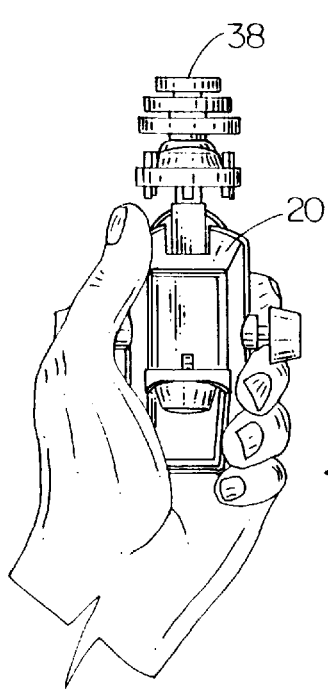
FIG. 2 is a front elevation view of the hand-held dental articulator of FIG. 1, being held in the palm of an operator's hand.
Figure 3:
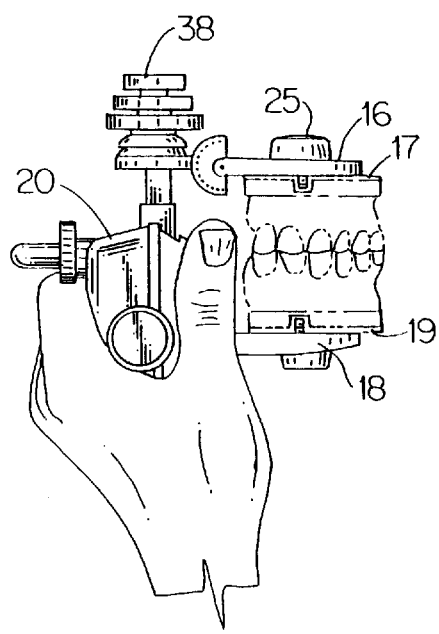
FIG. 3 is a side elevation view of the hand-held dental articulator of FIG. 1, being held in the palm of an operator's hand.

Referring now to FIGS. 2 and 3, articulator 10 is shown held in an operator's hand. FIGS. 2 and 3 are intended to illustrate how natural articulator 10 can be cradled in the palm of the operator's hand during use. Note how housing 20 is appropriately sized to allow the operator's fingers to extend to the sides of the housing and comfortably manipulate adjustment knobs 34. Also, other components, such as adjustment wheel 38, are readily accessible with the operator's other hand, for any necessary adjustments. Note in FIG. 3, articulator 10 is shown with the patient's dental models mounted to frames 16 and 18. This figure illustrates the metal mounting plates 17 and 19 (mentioned previously) which are incorporated as part of the dental casts during casting. Each of these plates contains a centrally located hole or bushing (not shown) through which mounting screws 24 are threaded, to clamp the casts securely to mounting frames 16 and 18.

Figure 4:
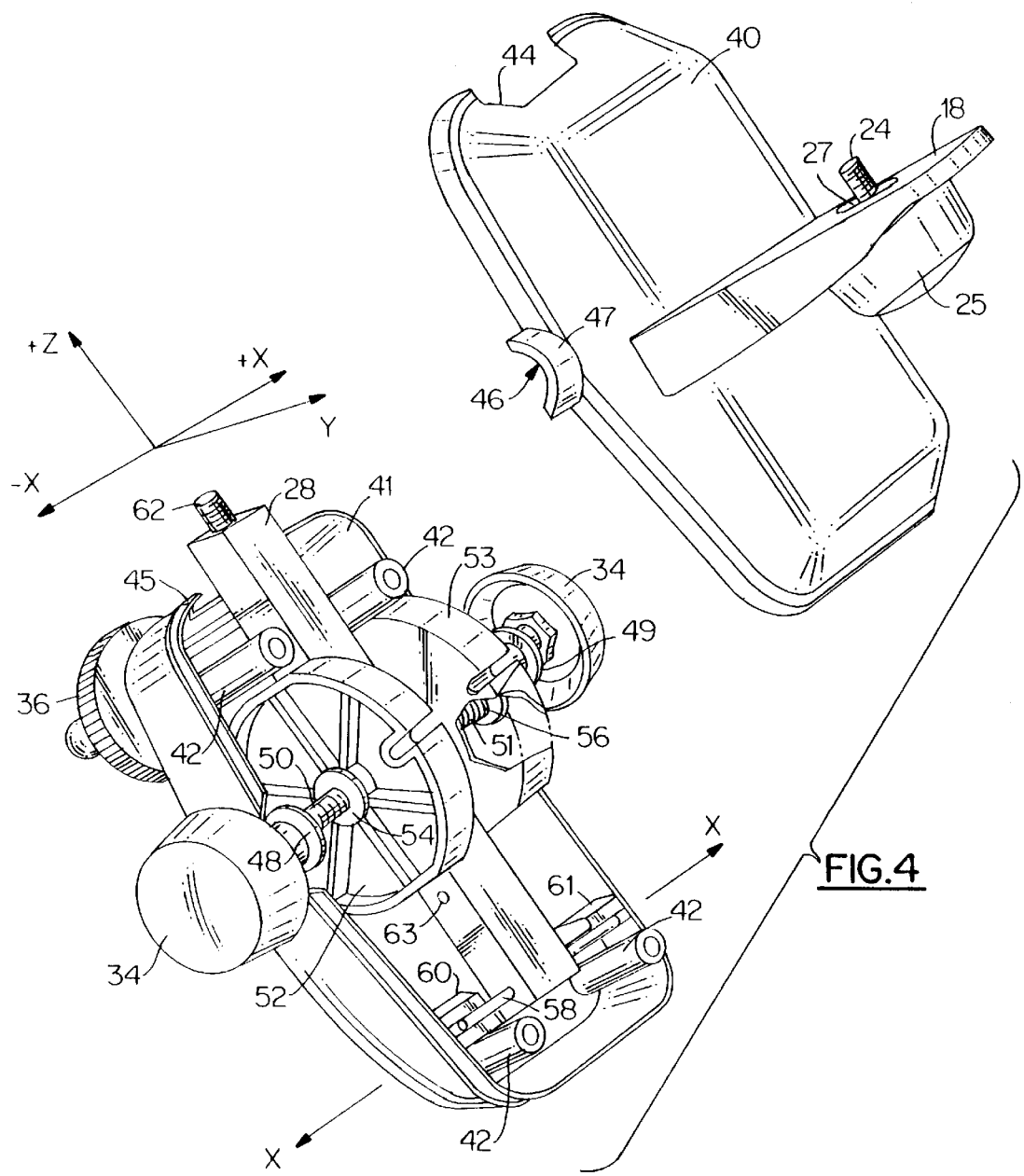
FIG. 4 is an exploded view of a housing of the hand-held dental articulator of FIG. 1, and showing the internal components of the articulator.

Referring now to FIG. 4, housing 20 comprises a front section 40 and a rear section 41. Lower mounting frame 18 is integrally formed as part of front section 40. Sections 40 and 41 may be injection molded parts, made from a durable and rigid plastic. Sections 40 and 41 are mounted together by four allen head screws (not shown) which are inserted through four holes, respectively, in rear section 41 (See FIG. 8). These holes project through four bushings 42, respectively (See FIGS. 4 and 7), molded on the inside of rear section 41. The allen head screws extend through bushings 42 and are threaded into a corresponding set of blind threaded bushings (not shown), molded on the inside of front section 40.

With further reference to FIG. 4, sections 40 and 41 contain recesses 44 and 45, respectively, which together form an aperture at the top of housing 20. This aperture provides an opening to allow positioning post 28 to extend therethrough. Contained on each side of sections 40 and 41 is a half-circle recess 46, bordered by a flange segment 47. When sections 40 and 41 are put together, recesses 46 and flange segments 47 form a flanged opening on each side of housing 20. Upon assembly, a pair of bushings 48 and 49 are seated tightly in the flanged openings, respectively.

Figure 7:
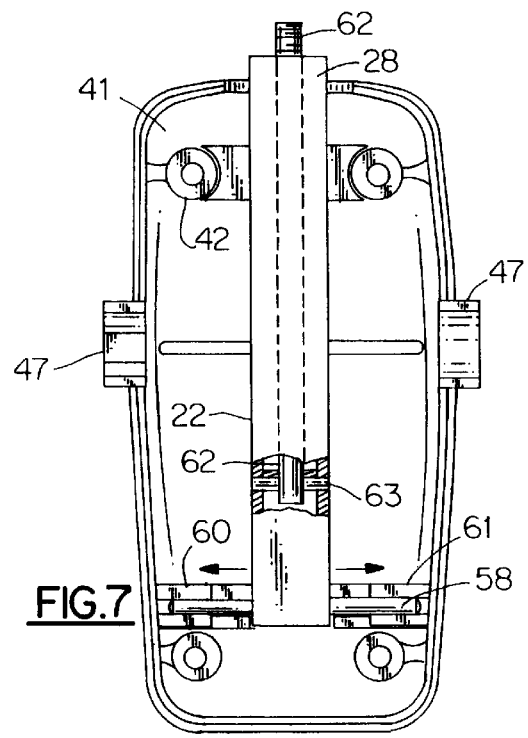
FIG. 7 is a front elevation view of the rear housing section of FIG. 6.

Further, upon assembly, a pair of push-pull rods 50 and 51 extend through bushings 48 and 49, respectively, and the proximal ends of rods 50, 51 are threaded tightly (or fixedly attached) to adjustment knobs 34. The distal ends of rods 50 and 51 are mounted to a pair of clamping plates 52 and 53, respectively, by way of push-pull hubs 54. Hubs 54 are fixedly mounted to the distal ends of rods 50, 51, respectively. Each hub 54 is rotatably seated in a center hole, tapped through its associated clamping plate (52 or 53). The external rim of each hub is actually a split washer seated in a circumferential groove in the push-pull rods (50, 51). In this embodiment, bushing 48 and rod 50 are thread, and rod 50 is threaded through bushing 48. This arrangement permits the manual push-pull adjustment of clamping plate 52, similar to the operation of a vice clamp. Bushing 49, on the other hand, is not threaded, and rod 51 is allowed to freely slide through it. Clamping plate 53 is urged or pushed toward the center of the housing by a compression spring 56, which is slipped onto rod 51 and compressed between bushing 49 and clamping plate 53. In an alternative embodiment, both bushings and push-pull rods may be threaded to allow manual knob adjustment of both clamping plates. As shown in FIG. 4, positioning member 22 extends into and through the clamping mechanism which, in this embodiment, is defined by knobs 34, bushings 48 and 49, rods 50 and 51, clamping plates 52 and 53, and hubs 54. As shown in FIGS. 4 and 7, positioning member 22 is coupled to housing 20 by a pin 58. Pin 58 is inserted through and slidably engages post 28. Pin 58 is seated in a pair of recesses contained in blocks 60 and 61. A complementary pair of recesses is contained in front section 40 (not shown), which registers with the recesses in blocks 60, 61, to contain pin 58. As a result of this arrangement, positioning member 22 is pivotally coupled to housing 20.

It is now understood from FIG. 4, that the position of positioning member 22 may be adjusted along the X-axis by working the clamping mechanism. It is also understood from FIG. 4 that positioning member 22 may be locked or secured into position by clamping plates 52 and 53. In an alternative embodiment, the recesses containing pin 58 may have an elongated or slotted cross section, allowing pin 58 to move linearly along the Y-axis (in and out of the paper, in FIG. 4). In such alternative embodiment, it is understood from FIG. 4 that positioning member 22 may be adjusted and secured into position along the Y-axis, using the clamping mechanism. The general theory of operation of positioning member 22 and the clamping mechanism are described in U.S. Pat. No. 5,743,733 (1998) to Crosland, the specification and drawings of which are incorporated herein by reference.

Figure 6:
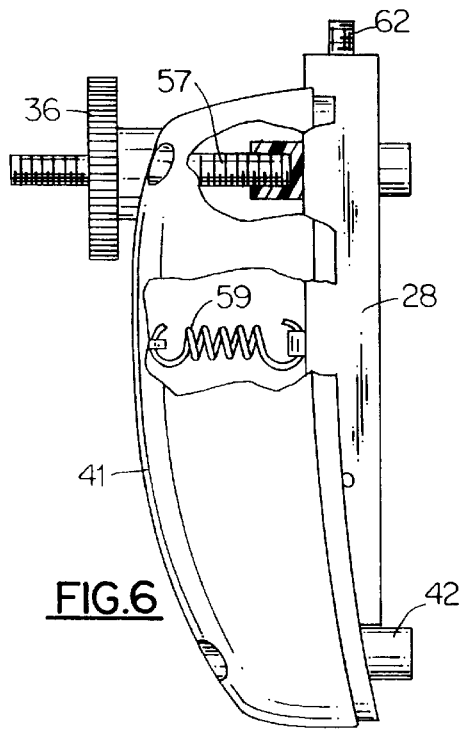
FIG. 6 is a partially cut-a-way, side elevation view of a rear housing section of the hand-held dental articulator of FIG. 1, showing various components associated with the positioning member.

With further reference to FIG. 4, positioning member 22 pivots along the Y-axis, rather than moves strictly, linearly along the Y-axis. Approximate linear motion along the Y-axis is achieved, however, because the usable range of positional adjustments along the Y-axis is not extensive. Y-axis displacement of positioning member 22 is accomplished in this embodiment by a threaded plunger 57 (See FIG. 6) which is adjusted along the Y-axis by turning threaded adjustment wheel 36. Plunger 57 is in contact with the rear surface of post 28, and urges post 28 (and thus member 22) forward along the Y-axis. As shown in FIG. 6, a tension spring 59 is hooked between the rear surface of post 28 and rear section 41, biasing member 22 in the negative Y-axis direction (See coordinates in FIG. 4). As shown in FIG. 4, housing 20 substantially encloses positioning member 22 and the clamping mechanism.

Figure 5:
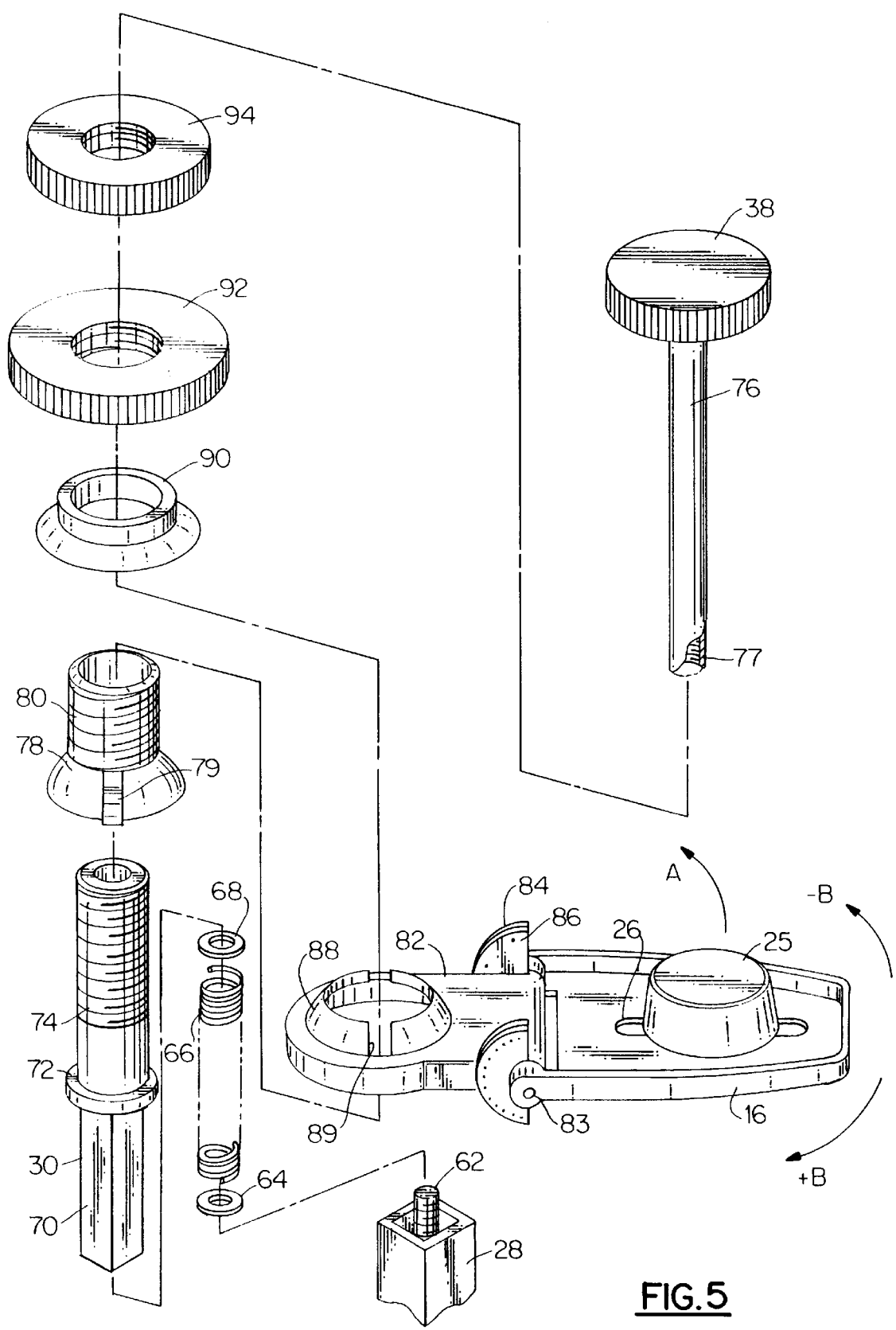
FIG. 5 is an exploded view of the positioning member of the hand-held dental articulator of FIG. 1, and showing the components for coupling the positioning member to the upper mounting frame of the articulator.

The construction of positioning member 22 will now be described in greater detail with reference to FIGS. 4, 5 and 7. Positioning post 28 is a square tube containing a threaded "Z-axis adjustment" rod 62. Rod 62 is mounted inside post 28 with a pin 63 (See cut-a-way in FIG. 7). Inside post 28, rod 62 extends through a flat washer 64, a compression spring 66, and a flat washer 68 (FIG. 5). Washer 64 rests on pin 63, spring 66 rests on washer 64, and washer 68 rests on spring 66. Plunger 30 (FIG. 5) includes a plunger tube 70, a stop flange 72, and a male tubular fitting 74 with external threads 75. Plunger tube 70 slidably engages the inside walls of post 28, and rests on washer 68. Rod 62 extends into plunger 30 where it is accessible by a threaded stem 76 (FIG. 5). Stem 76 is fixedly attached to adjustment wheel 38, and has internal threads 77.

The coupling of positioning member 22 to upper mounting frame 16 will now be described in greater detail with reference to FIG. 5. In the preferred embodiment, the coupling of member 22 to upper mounting frame 16 is a dynamic coupling. As shown in FIG.5, a spherical bearing 78 includes a pair of oppositely disposed key members 79 and external threads 80. Bearing 78 slidably engages fitting 74 and rests on flange 72.

Upper mounting frame 16 is pivotally attached to a coupling member 82 by means of a hinge pin 83. This pivotal attachment permits frame 16 to be manually elevated upward (See arrow A) from an initial rest position (shown in FIG.5) and lowered to the initial rest position. As shown in FIG. 5, frame 16 and coupling member 82 both have a pair of index members 84 and 86, respectively. Index members 84 rotate about pin 83 when frame 16 is elevated upward from the rest position, thus providing means for gauging the upward displacement of frame 16. A pair of wedge stops (not shown) on the bottom surface of frame 16 makes contact with index members 86 (of coupling member 82) at the rest position, thus stopping the downward movement of frame 16 at the rest position.

Coupling 82 includes a spherical bearing portion 88 that contains a pair of key slots 89. Bearing portion 88 fits over bearing 78, and both parts are locked together in rotation by means of keys 79 and key slots 89. The assembly of bearing 88 over bearing 78 creates a ball joint between coupling 82 and positioning member 22. A clamping cap 90 slidably engages fitting 80 and is seated on top of bearing portion 88. A threaded locking wheel 92 is threaded onto fitting 80. As wheel 92 tightens on fitting 80, it bears down onto the assembly of cap 90, bearing 88, and bearing 78. This results in locking the ball joint (created by bearings 78 and 88). As wheel 92 loosens on fitting 80, coupling 82 and frame 16 are free to move about the ball joint. This movement is referred to as the "pilot" movement.

As shown in FIG. 5, a threaded wheel 94 is threaded onto fitting 74. As wheel 94 tightens on fitting 74, wheel 94 bears down onto bearing 78 which, in turn, bears down on flange 72. In the final assembly, fitting 80 projects slightly through wheel 92, so that contact between bearing 78 and wheel 94 is possible. Bearing 78 is prevented from rotating along the paths represented by arrows B, –B in FIG. 5 (i.e., about the Z-axis), when wheel 94 is tightened on fitting 74. Thus, rotational (or "lateral") movement of frame 16 is prevented by tightening wheel 94. Wheel 94 allows one to adjust the rotational position of frame 16, along paths B, –B, and lock frame 16 into a desire rotational position. Rotational positioning may be referred to as lateral positioning, because such rotational movement simulates the lateral excursions of the upper jaw.

With further reference to FIG. 5, internal threads 77 of stem 76 engage the external threads of rod 62. As stem 76 is threaded onto rod 62 (e.g., by turning wheel 38 clockwise), wheel 38 eventually bears down on plunger 30 which, in turn, bears down on washer 68 and spring 66. In the final assembly, fitting 74 projects slightly through wheel 94, so that contact between plunger 30 and wheel 38 is possible. This arrangement provides smooth positional adjustment of frame 16 along the Z-axis (or "in the vertical direction").

Figure 8:
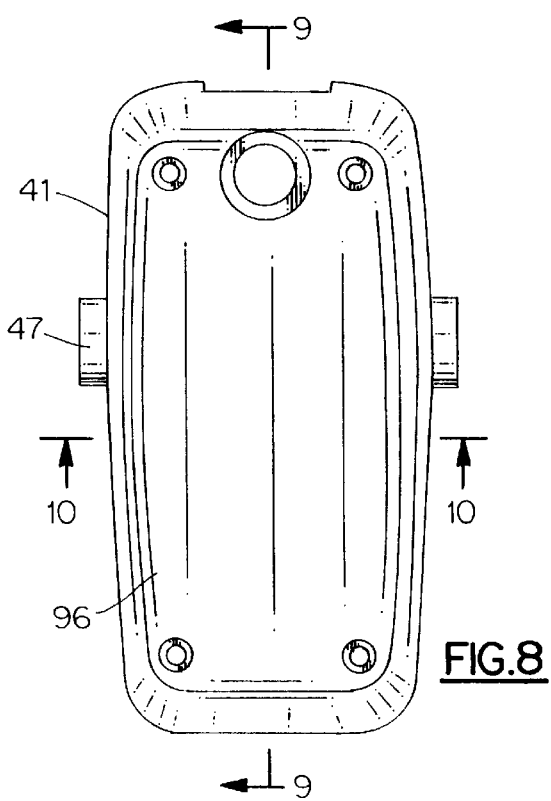
FIG. 8 is a rear elevation view of the rear housing section of FIG. 6, with the rear adjustment wheel removed.
Figure 9:
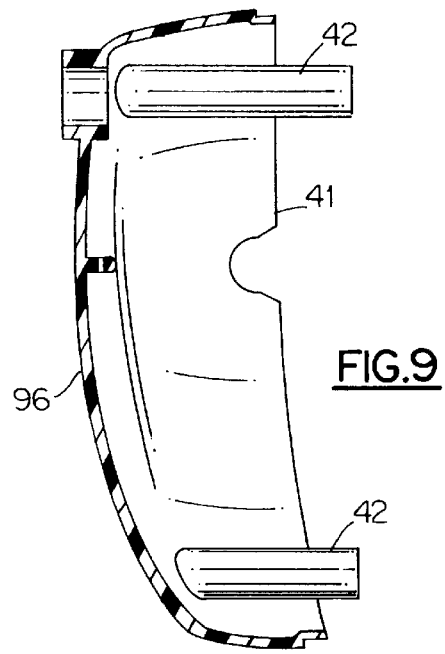
FIG. 9 is a cross sectional view of the rear housing section, taken along line 9—9 in FIG. 8.
Figure 10:
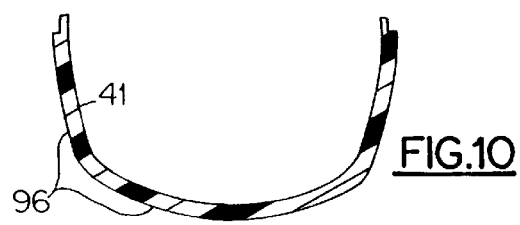
FIG. 10 is a cross section of the rear housing section, taken along line 10—10 in FIG. 8.

Referring now to FIGS. 8–10, rear section 41 of housing 20 includes a manual surface 96. Manual surface 96 is that portion of the exterior surface of section 41 which normally makes contact with the palm of the hand (See, e.g., FIGS. 2 and 3). As shown in FIGS. 9 and 10, surface 96 is curved in both sectional dimensions, and is preferably configured and dimensioned to fit an average adult, human palm. In the preferred embodiment, the shape of surface 96 is configured to substantially conform to the curvature of the palm, and should substantially conform to the size of the palm.

While the preferred embodiments of the invention have been particularly described in the specification and illustrated in the drawings, it should be understood that the invention is not so limited. Many modifications, equivalents and adaptations of the invention will become apparent to those skilled in the art without departing from the spirit and scope of the invention, as defined in the appended claims.

What I claim is:

1. A hand-held dental articulator, comprising:
   a first frame, configured to accept for mounting thereto a first dental model;
   a second frame, configured to accept for mounting thereto a second dental model; and
   a support structure, coupled to said first and said second frames, and configured to support said first frame in opposing and overlapping relationship with said second frame, said support structure including a manual surface that substantially conforms to the curvature of an operator's palm,
   whereby said hand-held dental articulator is easily and comfortably held in the operator's hand during use.

2. The hand-held dental articulator of claim 1, wherein the manual surface of said support structure substantially conforms to the size of the operator's palm.

3. The hand-held dental articulator of claim 1, wherein said support structure is configured and dimensioned to substantially fit in the operator's palm.

4. The hand-held dental articulator of claim 1, wherein said support structure includes a housing and the manual surface of said support structure is a surface of the housing.

5. The hand-held dental articulator of claim 4, wherein the housing of said support structure is configured and dimensioned to substantially fit in the operator's palm.

6. The hand-held dental articulator of claim 1, wherein said support structure further includes
   a positioning member having one end coupled to said first frame, and
   clamping means, into which the positioning member extends, for allowing adjustment of the position of the positioning member and for securing the positioning member in an adjusted position,
   whereby the position of said first frame relative to said second frame is adjustable by adjusting the position of the positioning member.

7. The hand-held dental articulator of claim 6, wherein said support structure further includes
   a housing that substantially encloses the positioning member and the clamping means, the manual surface of said support structure being a surface of the housing.

8. The hand-held dental articulator of claim 6, wherein the positioning member of said support structure extends through the clamping means of said support structure.

9. A dental articulator apparatus, comprising the hand-held dental articulator of claim 1, and further comprising a base containing a recess which is configured and dimensioned to support said hand-held articulator at a pitch angle that is convenient for viewing dental models mounted to said articulator.

10. A hand-held dental articulator, comprising:
    a lower mounting member, configured to accept for mounting thereto a lower dental model;
    an upper mounting member, configured to accept for mounting thereto an upper dental model;
    a support structure, coupled to said lower and said upper mounting members, and configured to support said upper mounting member in opposing and overlapping relationship with said lower mounting member, said support structure including a manual surface that substantially conforms to the curvature of an operator's palm,
    whereby said hand-held dental articulator is easily and comfortably held in the operator's hand during use.

11. A hand-held dental articulator, comprising:
    a first frame configured to accept for mounting thereto a first dental model;
    a second frame configured to accept for mounting thereto a second dental model;
    a positioning member having one end coupled to said first frame, and configured and dimensioned to position said first frame in opposing and overlapping relationship with said second frame;
    clamping means, into which said positioning member extends, for allowing adjustment of the position of said positioning member and for securing said positioning member in an adjusted position, whereby the position of said first frame relative to said second frame is adjustable by adjusting the position of said positioning member; and
    a housing substantially enclosing said positioning member and said clamping means, said second frame being attached to said housing, said housing including a manual surface that substantially conforms to the curvature of an operator's palm,
    whereby said hand-held dental articulator is easily and comfortably held in the operator's hand during use.

12. The hand-held dental articulator of claim 11, wherein the manual surface of said housing substantially conforms to the size of the operator's palm.

13. The hand-held dental articulator of claim 11, wherein said housing is configured and dimensioned to substantially fit in the operator's palm.

* * * * *